United States Patent
Siegal

(10) Patent No.: US 7,503,920 B2
(45) Date of Patent: Mar. 17, 2009

(54) SPINAL SURGERY SYSTEM AND METHOD

(76) Inventor: Tzony Siegal, 23, Moshav Shoeva (IL)

( * ) Notice: Subject to any disclaimer, the term of this patent is extended or adjusted under 35 U.S.C. 154(b) by 702 days.

(21) Appl. No.: 11/028,655

(22) Filed: Jan. 5, 2005

(65) Prior Publication Data

US 2006/0036273 A1    Feb. 16, 2006

Related U.S. Application Data

(63) Continuation-in-part of application No. 10/915,478, filed on Aug. 11, 2004, now abandoned.

(51) Int. Cl.
*A61B 17/56* (2006.01)
(52) U.S. Cl. .................. 606/79; 606/87; 606/99
(58) Field of Classification Search ........... 606/61, 606/79, 80, 84, 92, 93, 167, 170, 179, 87, 606/96, 99
See application file for complete search history.

(56) References Cited

U.S. PATENT DOCUMENTS 5,695,513 A * 12/1997 Johnson et al. ............. 606/180

| | | |
|---|---|---|
| 2005/0060036 A1 | 3/2005 | Schultz et al. |
| 2005/0273166 A1 | 12/2005 | Sweeney |
| 2006/0142858 A1 | 6/2006 | Colleran et al. |
| 2006/0247781 A1 | 11/2006 | Francis |

FOREIGN PATENT DOCUMENTS

| DE | 202006005868 | 6/2006 |
|---|---|---|
| WO | WO2006/072941 | 7/2006 |

* cited by examiner

*Primary Examiner*—Eduardo C Robert
*Assistant Examiner*—David Comstock
(74) *Attorney, Agent, or Firm*—Mark M. Friedman

(57) ABSTRACT

Apparatus and method for minimally invasive spinal surgery employs an elongated flexible guide element inserted so as to pass in through a first lateral posterior incision, through the spinal column anterior to the spinal cord, and out through a second lateral posterior incision contralateral to said first incision. The guide element is used to guide various elements to a desired position within the spinal column as part of the surgical procedure. Preferably, two hollow rigid tubes rigidly coupled outside the body in converging relation are used to define a working gap within the spinal column through which the guide element passes. This provides a platform for manipulation of tissues and introduction of implants anterior to the spinal cord. Procedures described include reinforcement of a degenerative intervertebral disc and restoration of a damaged vertebral body.

20 Claims, 9 Drawing Sheets

FIG. 5
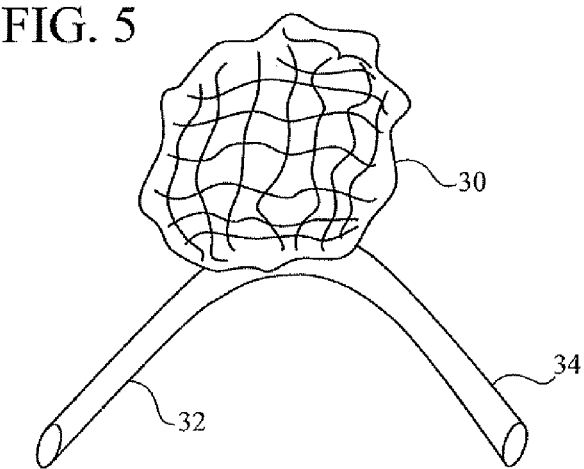
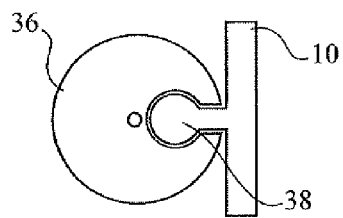
FIG. 6
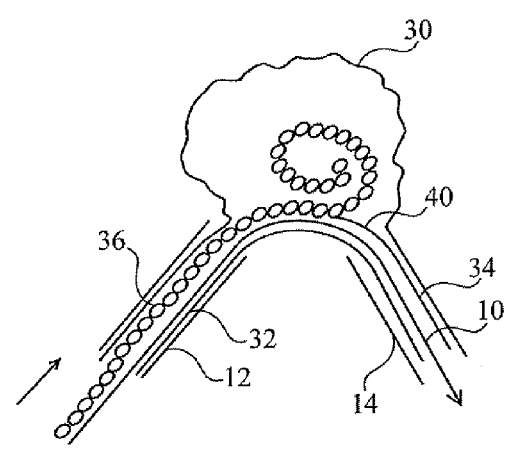
FIG. 7

SPINAL SURGERY SYSTEM AND METHOD

This application is a Continuation-In-Part of Ser. No. 10/915,478 filed Aug. 11, 2004 now abandoned.

FIELD AND BACKGROUND OF THE INVENTION

The present invention relates to spinal surgery and, in particular, it concerns a system and method for performing various minimally invasive spinal surgical procedures.

The past several years have witnessed a multitude of novel ideas and techniques for improved care for patients with spinal conditions. Some of these advances have improved the quality of life of patients suffering from degenerative disk disease with disabling low back pain. The current trend is towards less invasive approaches with less iatrogenic soft-tissue morbidity, as compared to traditional procedures with or without fusion of vertebral bones.

Despite a wide range of procedures performed today as minimally invasive spinal surgery ("MISS") procedures, there remain fundamental limitations to the available options in a number of respects. Firstly, while a posterior approach is preferred for minimizing iatrogenic soft-tissue morbidity, it has been found difficult to achieve precise positioning of devices anterior to the spinal cord using a posterior approach. Furthermore, the available techniques for anchoring implants in position within the spinal column are limited in their reliability and tend to generate problematic local debris.

There is therefore a need for an apparatus and method for minimally invasive spinal surgery which would provide a guide element for providing a well defined reference location within the spinal column for performance of a MISS procedure anterior to the spinal cord.

SUMMARY OF THE INVENTION

The present invention is an apparatus and method for minimally invasive spinal surgery, and corresponding surgical techniques which can advantageously be implemented using the apparatus and method of the invention. The invention also relates to a tunneling system and corresponding method for forming an arcuate tunnel through tissue.

According to the teachings of the present invention there is provided, a tunneling system for forming an arcuate tunnel through biological tissue, the tunneling system comprising: (a) a delivery conduit having an inner channel and an open end, at least part of the inner channel being substantially straight; and (b) a tunneling device for deploying within the inner channel and advancing beyond the open end, at least a distal portion of the tunneling device being formed from a series of substantially rigid elements interconnected at pivotal interconnection regions having parallel effective hinge axes, the interconnection regions being configured to transfer compressive forces between adjacent of the elements, each of the elements further including at least one contact surface disposed for abutting a corresponding region of an adjacent one of the elements so as to define a maximum deflection of relative pivotal motion between adjacent of the elements, such that, when the distal portion is deployed within the inner channel, at least part of the distal portion assumes a substantially straight state with the contact surfaces and the corresponding regions separated and, as the distal portion is advanced beyond the open end into the biological tissue, the elements are deflected to the maximum deflection so that a part of the distal portion beyond the open end assumes a pre-defined substantially arcuate state.

According to a further feature of the present invention, the tunneling device is integrally formed as an elongated body with a plurality of transverse slots spaced along its length, regions between adjacent of the slots providing the substantially rigid elements and regions around the slots providing the pivotal interconnection regions.

According to a further feature of the present invention, the elongated body is formed from metallic material.

According to a further feature of the present invention, the elongated body is hollow.

According to a further feature of the present invention, at least a distal tip of the elongated body is non-hollow.

According to a further feature of the present invention, the elongated body has a substantially rectangular cross-sectional outline.

According to a further feature of the present invention, the transverse slots are substantially V-shaped.

According to a further feature of the present invention, the transverse slots are substantially parallel-sided.

According to a further feature of the present invention, each of the elements includes at least two of the contact surfaces and a corresponding two abutment regions, the at least two contact surfaces being non-coplanar.

According to a further feature of the present invention, the tunneling device terminates in a distal tip having a bevel angle inclined so as to tend to deflect the elements towards the arcuate state when advanced.

According to a further feature of the present invention, the bevel angle is inclined between 20° and 70° to a longitudinal axis of the tunneling device when in the substantially straight state.

According to a further feature of the present invention, there is also provided a drive device associated with the delivery conduit and with the tunneling device, the drive device being configured to advance the tunneling device relative to the delivery conduit.

According to a further feature of the present invention, the tunneling device features a series of recesses, the drive device having at least one projecting feature for engaging at least one of the recesses.

According to a further feature of the present invention, the tunneling device further includes a tensioning element deployed along at least part of a length of the tunneling device for biasing adjacent of the elements to the maximum deflection.

There is also provided according to the teachings of the present invention, an apparatus for use in performing a minimally invasive spinal surgical procedure via a pair of bilateral stab wounds on either side of a subject region of the spine of a patient, the apparatus comprising: (a) a first hollow rigid tube having a proximal end and a distal end, the distal end for insertion through a first of the stab wounds; (b) a second hollow rigid tube having a proximal end and a distal end, the distal end for insertion through a second stab wound in the back of a patient; (c) a rigid coupling for rigidly coupling the first and second tubes such that the tubes converge towards the distal ends but maintain a predefined gap between the distal ends; and (d) a tunneling system deployable along the first tube for forming an arcuate tunnel so as to traverse the gap between the distal ends of the first and second tubes, the tunneling system including a tunneling device, at least a distal portion of the tunneling device being formed from a series of substantially rigid elements interconnected at pivotal interconnection regions having parallel effective hinge axes, the interconnection regions being configured to transfer compressive forces between adjacent of the elements, each of the elements further including at least one contact surface disposed for abutting a corresponding region of an adjacent one of the elements so as to define a maximum deflection of relative pivotal motion between adjacent of the elements, such that, when the distal portion of the tunneling device is deployed within the first tube, at least part of the distal portion assumes a substantially straight state with the contact surfaces and the corresponding regions separated and, as the distal portion of the tunneling device is advanced beyond the distal end, the elements are deflected to the maximum deflection so that a part of the distal portion of the tunneling element beyond the distal end of the first tube assumes a pre-defined substantially arcuate state.

According to a further feature of the present invention, there is also provided an elongated flexible guide element for deployment, after removal of the tunneling system, so as to extend through the first hollow tube from the proximal end to the distal end, to traverse the gap and to extend through the second hollow tube from the distal end to the proximal end.

According to a further feature of the present invention, the first and second tubes are implemented as substantially straight hollow tubes.

According to a further feature of the present invention, the distal ends of the first and second tubes are implemented as inward-facing beveled ends.

According to a further feature of the present invention, the distal ends of the first and second tubes are curved towards the gap.

According to a further feature of the present invention, there is also provided a removable trocar removably receivable within each of the first and second tubes for facilitating insertion of the first and second tubes in the back of the patient.

BRIEF DESCRIPTION OF THE DRAWINGS

The invention is herein described, by way of example only, with reference to the accompanying drawings, wherein:

FIG. 5 is a schematic plan view of a preferred net element for use in the procedure of FIG. 3;

FIG. 6 is a schematic cross-sectional view showing a preferred mode of releasable connection of beads with a flexible guide element for use in the procedure of FIG. 3;

FIG. 7 is a schematic plan view illustrating the release of a chain of beads into the net element of FIG. 4 during performance of the procedure of FIG. 3;

DESCRIPTION OF THE PREFERRED EMBODIMENTS

The present invention is an apparatus and method for minimally invasive spinal surgery. The invention also provides surgical techniques, advantageously implemented using the apparatus and method of the invention, for intervertebral disc repair and for vertebral body repair.

The principles and operation of a surgical apparatus and method, and surgical techniques, according to the present invention will be better understood with reference to the drawings and the accompanying description.

Surgical Apparatus and Method

Figure 1:
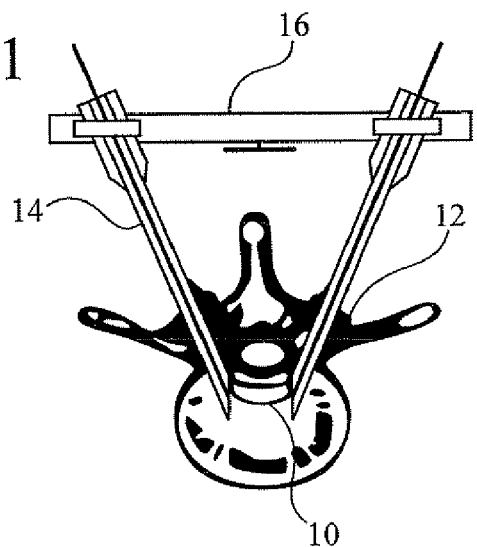
FIG. 1 is a plan view of a vertebra illustrating schematically a surgical apparatus and method, constructed and operative according to the teachings of the present invention.

Referring now to the drawings, FIG. 1 illustrates a preferred apparatus and corresponding method for performing various minimally invasive spinal surgery (MISS) procedures according to the teachings of the present invention. In general terms, the preferred surgical method of the present invention is based on inserting an elongated flexible guide element 10 such that the guide element passes in through a first lateral posterior incision, passes through the spinal column anterior to the spinal cord, and passes out through a second lateral posterior incision contralateral to the first incision. The guide element 10 is then employed to guide at least one element to a desired position within the spinal column as part of the surgical procedure.

It will be immediately apparent that the present invention offers profound advantages for performance of MISS procedures. Specifically, the guide element thus placed functions in a manner analogous to the ubiquitous guide wire of vascular surgery, defining a precise path along which other elements or devices can be advanced in a precise and repeatable manner. The device effectively provides a platform for manipulation of tissues and introduction of implants anterior to the spinal cord. The elements or devices may travel along using the guide element as a stationary rail, or the guide element itself may be advanced through the spinal column with pull-through functionality. In either case, the guide element provides a well defined reference location within the spinal column for performance of a MISS procedure. In the case of implanted devices, the guide element also facilitates bilateral fixation at the end of the procedure by attachment of portions of the guide element to bone surfaces on both sides of the vertebra. These and other advantages of the present invention will be better understood from the following detailed description.

Turning now to structural details of a preferred implementation of the present invention, the path of guide element 10 through the spinal column is preferably defined by a pair of hollow rigid tubes 12, 14 inserted through contra-lateral incisions in the back of a subject. For simplicity of representation, the soft tissue through which the incisions are made has been omitted from the drawings. Suitable incisions for such a lateral posterior approach are well known, and can typically be implemented as a small stab wound. A rigid coupling 16 is configured for rigidly coupling tubes 12, 14 such that the tubes converge towards their distal (inserted) ends but maintain a predefined gap between their ends. This gap is preferably in the range of 15-20 millimeters wide. Guide element 10 is then deployed passing in through a first of the hollow tubes 12, traversing the gap between the distal ends, and passing out through a second of the hollow tubes 14. The portion of the guide element traversing the gap defines a working region within the spinal column, as will become clearer from the subsequent examples.

Figure 2:
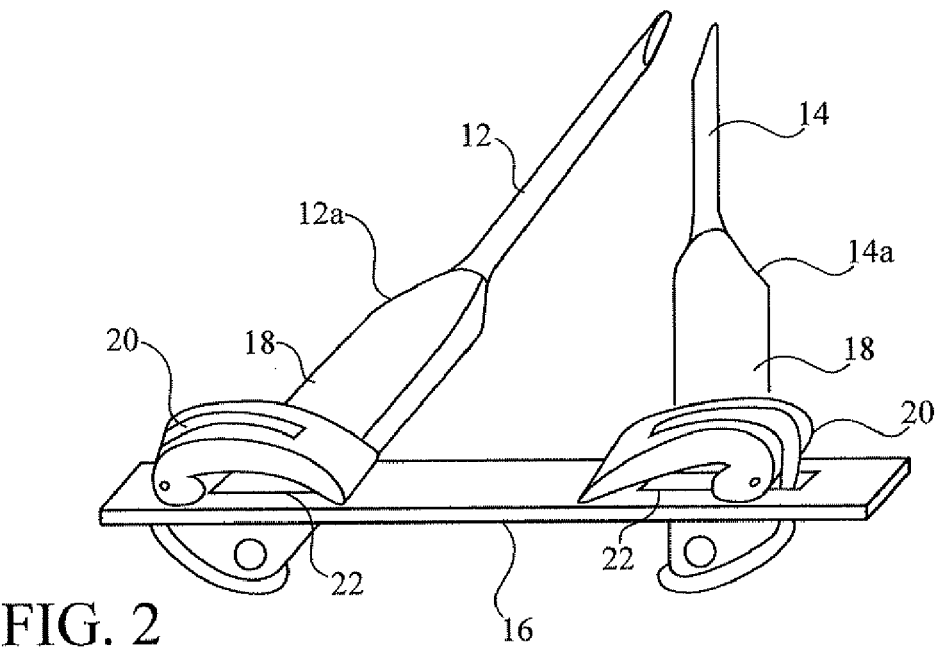
FIG. 2 is a schematic isometric view of the apparatus of FIG. 1.
Figure 3A:
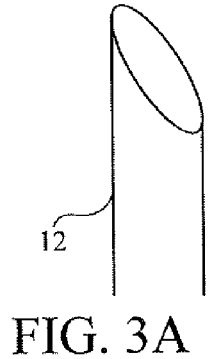
FIG. 3A is an enlarged side view of a first preferred configuration for the distal end of rigid tubes for use in the apparatus of FIG. 1.
Figure 3B:
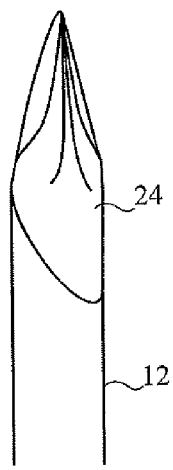
FIG. 3B is an enlarged side view of the distal end of the tube of FIG. 3A showing a trocar inserted within the tube for penetration of tissue.
Figure 3C:
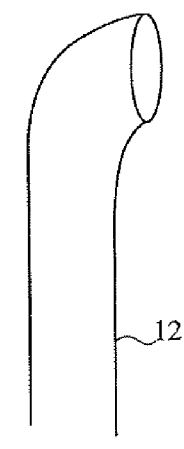
FIG. 3C is a side view of an alternative configuration for a distal end of rigid tubes for use in the apparatus of FIG. 1.

FIG. 2 illustrates in more detail a preferred implementation of the apparatus. Specifically, first and second tubes 12, 14 are preferably implemented as substantially straight hollow tubes with inward-facing distal openings such that the distal openings face each other across the gap. This facilitates insertion of guide element 10 passing across the gap and helps to clearly delimit the sides of the gap. In a first preferred implementation shown here, and enlarged in FIG. 3A, the distal ends of tubes 12, 14 are implemented as inward facing beveled ends. In an alternative preferred implementation, the distal ends of first and second tubes 12, 14 are curved towards the gap as illustrated in FIG. 3C.

In order to ensure that the beveled or curved distal ends of tubes 12, 14 are correctly oriented, at least a proximal clamping portion of each tube is preferably formed so as to be asymmetrical under rotation and to cooperate with clamping elements associated with rigid coupling 16 so as to define the required orientation. Thus, in the example shown here, each tube 12, 14 has an enlarged clamping portion 12a, 14a with a flat surface 18 defining a clamping orientation relative to rigid coupling 16. Clamping portions 12a and 14a are preferably also asymmetric under reflection so as to be non-interchangeable with each other. Thus, in the example shown here, each clamping portion has a generally triangular asymmetric cross-section where only one side is flat to provide clamping surface 18 and the remainder of the surfaces are curved.

In the particularly simple implementation shown here, rigid coupling 16 is implemented with eccentric lever clamps 20 deployed in slots 22. This allows quick clamping in a range of relative spacings between the rigid tubes, but in a predefined angular relation defined by clamping surfaces of clamps 20. The angular relation is typically inclined inwards towards a central plane through the device at between 15°-25°, corresponding to an angle of conversion of the two tubes in the range of 30°-50°. Clearly, many other clamping configurations may equally be used, optionally giving additional degrees of freedom of adjustment such as an angular adjustment of the rigid tubes.

Although shown here as a free-standing structure, rigid coupling 16 may be mechanically linked through an adjustable clamping structure (not shown) to a fixed reference surface such as an operating table to provide additional stabilization and rigidity during performance of a procedure. Alternatively, the rigid coupling may be temporarily anchored to the subject's body via axial skeletal features. Suitable adjustable clamping structures for both of these types of clamping are known in the art and will not be described herein.

A wide range of materials may be used to produce rigid tubes 12, 14 and rigid coupling 16. Particularly preferred examples include, but are not limited to, surgical steel and other biocompatible metals, metal alloys and rigid polymers. The diameter of the tubes is typically in the range of 2-6 mm, and most preferably in the range of 3-5 mm.

According to a further optional feature particularly relevant to the beveled-ended implementation, a removable trocar 24 is removably received within each tube 12, 14 (FIG. 3B) to facilitate insertion of the first and second tubes through soft tissues of the subject's back to reach the desired position. The trocar is then withdrawn to free the lumen of the tube for insertion of the guide element.

Figure 4:
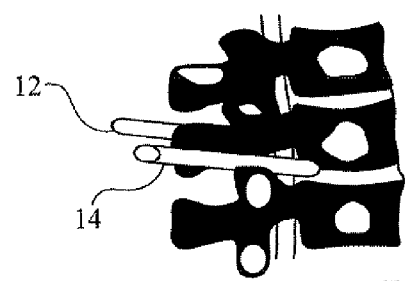
FIG. 4 is a schematic side view illustrating the use of the apparatus of FIG. 1 employed to perform a procedure on an intervertebral disc.

It should be noted that the apparatus and method of the present invention are useful for performance of a wide range of MISS procedures, including many known procedures conventionally performed by other surgical techniques. These include procedures performed both on intervertebral discs and on the vertebral body. In the case of an intra-discal procedure, rigid tubes 12, 14 are preferably inserted immediately above the transverse processes of the vertebra below the disc in question as shown in FIG. 4. In the case of an intra-vertebral procedure, preferred positioning for insertion of rigid tubes 12, 14 is via small holes drilled through the pedicle on each side of the vertebra.

Figure 3D:
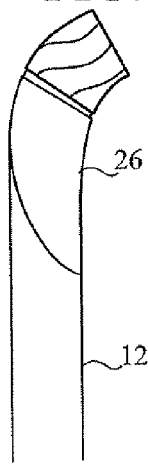
FIG. 3D is an enlarged side view showing a directional drilling device extending from the distal tube end of FIG. 3A.

Depending upon the nature and current status of the tissue (disc nucleus or vertebral body cancellous bone) in the gap between the distal ends of the rigid tubes, it may be possible to insert guide element 10 across the gap simply be advancing it along one of the tubes, optionally with either a steering mechanism or a with a tip with a pre-formed curvature to facilitate the lateral motion required to cross the gap to reach the opening of the other tube. In other cases, however, a tunneling device may be required. For this purpose, the apparatus preferably also includes a retractable tunneling or drilling system. A particularly preferred implementation of a tunneling system constructed and operative according to the teachings of the present invention will be described below with reference to FIGS. 10A-15. Alternatively, a conventional drilling device may be used such as drilling device 26 (FIG. 3D), removably associated with one of tubes 12, 14 so as to drill a connecting channel through the gap for insertion of the guide element. In this case, retractable drilling device 26 is preferably implemented as a directional drilling device configured for drilling in a direction non-parallel with a central bore of the tube. Although thermal or laser ablation may be used for this purpose, mechanical drills are believed to be preferable to avoid risk of thermal damage to surrounding tissue (disc, bone and nerves). Examples of suitable mechanical directional drilling devices, both steerable and with a fixed lateral curvature, are known in the field and will not be described herein in detail. By way of example, two suitable designs are described in U.S. Pat. No. 6,558,386 which is hereby incorporated by reference, particularly with reference to FIGS. 9-10 thereof.

Turning now to guide element 10 itself, it should be noted that the guide element may be implemented in many different configurations varying in shape, gauge, materials and deployment according to the requirements of each given procedure to be performed. Furthermore, various different guide element configurations may be used during the course of a single procedure, either by withdrawing a first guide element and deploying an alternative guide element or by connecting different guide element configurations sequentially such that each section pulled out draws the subsequent section of the guide element into position traversing the gap within the spinal column as required. In many cases, the guide element is preferably chosen to be asymmetric under rotations of less than 180° about its length, thereby providing a defined orientation for devices introduced within the spinal column. A simple example of a preferred asymmetric form is a flat strip. Other examples will be discussed below in the context of certain specific applications. Preferred materials for the guide element are typically flexible biocompatible polymer materials such as PEEK or resilient metals or metal alloys such as spring steel or superelastic nitinol alloys.

Intervertebral Disc Repair

Turning now to FIGS. 5-7, a preferred technique for repair of a damaged intervertebral disc will now be described. It should be appreciated that, while the technique is described in a particularly preferred context implemented using the surgical method of the present invention, various aspects of the technique are believed to be patentable in their own right even if implemented using otherwise conventional surgical methods.

In general terms, the disc repair technique of the present invention is performed by introducing into the nucleus of a damaged disc a plurality of beads of material chosen to have surface properties which encourage generation of scar tissue. By using beads, the filling conforms readily to the geometry of the load-transfer surfaces of adjacent vertebrae and immediate provides load-bearing support in a manner similar to that described in U.S. Pat. No. 5,702,454. At the same time, in contrast to the teachings of that patent, the use of surfaces for encouraging generation of scar tissue initiates a physiological process in which scar tissue fills the gaps between the beads, becoming a significant if not primary contributor to the physical properties of the disc nucleus. Scar tissue, being highly fibrous, moderately flexible and having few nerves has been found by the present inventor to be an ideal substitute for the natural tissue of the inner disc.

In order to encourage scar tissue formation, the beads are preferably formed primarily, or entirely, from material exhibiting surface pores of width 50-100 microns, and most preferably in the 70-80 micron range. A preferred but non-limiting example of a biocompatible material exhibiting pores of this size is polypropylene. The beads are preferably rounded to ensure that they conform readily to the shape of the space to be filled. Most preferably, substantially spherical beads are used. A preferred diameter (or maximum dimension for non-spherical beads) is typically in the range of 1-10 mm, and most preferably around 1-5 mm.

In order to ensure correct placement of the beads within the disc, this aspect of the present invention preferably employs a net element configured to contain the plurality of beads within a defined containment region. The net element must clearly have openings sufficiently fine to prevent passage of the filling beads. At the same time, in order to facilitate the aforementioned generation of scar tissue around the beads, the openings of the net element are sufficiently large to permit penetration of tissue cells and small blood vessels. A preferred range of sizes for the net element openings is up to about 0.5 mm.

A preferred implementation of net element for use in the surgical method and apparatus described above is shown in FIG. 5 designated 30. In this case, net element 30 is attached to, or integrally formed with, an opening in the side of a piece of flexible tubing such that the portions either side of the net element provide first and second tubular flexible elongated fixation appendages 32 and 34. The functions of these appendages will be described below.

The guide element surgical method and apparatus described above offers a particularly convenient, controllable and effective manner of delivering a desired quantity of beads into the intervertebral disc. Specifically, as illustrated schematically in FIG. 6, a series of beads 36 are preferably configured to be detachably associated with an appropriately formed guide element 10 and to be released from the guide element for delivery to a desired position within the intervertebral disc. In the implementation illustrated in FIG. 6, each bead 36 is formed with a shaped recess and elongated guide element 10 is formed with a complementary sequence of projections or projecting ridge 38 forming a releasable "snap" connection. Clearly, alternative releasable connection configurations may also be used. Other examples include, but are not limited to, reverse configurations with projections from beads 36 engaging recessed in guide element 10, and integrally molded implementations where beads 36 and guide element 10 are integrally molded with small frangible attachment points which can be broken to release the beads. To ensure release of the beads from the guide element at the correct location, net element 30 is preferably provided with a release configuration deployed to effect release of the beads from guide element 10. In the example shown here, the release configuration is implemented as a forked ramp or wedge 40 located within the net element near the point where guide element 10 passes out through appendage 34.

Most preferably, in order to further reduce the risk of beads escaping from the internal disc volume, beads 36 are interconnected into strings or chains of beads by small interconnecting links. Typically, the links are integrally molded with the beads. Alternatively, the beads may be separately formed and then strung on a separate connecting strand.

In use, after positioning of rigid tubes 12, 14 and guide element 10 as described above, net element 30 is advanced in a folded state around guide element 10 until it reaches a position with the net deployed in the gap between the rigid tubes and appendages 32 and 34 deployed within tubes 12 and 14, respectively, as shown in FIG. 7. This positioning may be reliably determined by appropriate length markings on parts of appendages 32 and/or 34 extending outwards from the rigid tubes indicating the distance from the beginning of the net element. Additionally, or alternatively, imaging techniques such as fluoroscopy may be used to verify the positioning. For this purpose, radio-opaque reference markers are preferably incorporated into the net element at predefined positions.

Once the net element is in place, the portion of the guide element carrying beads 36 is advanced (typically pulled-through) to draw the beads into the internal volume of the net element. As they reach release configuration 40, the beads become detached from the guide element, thereby freeing a string of beads as shown in FIG. 7. Preferably, the deployment of the beads on guide element 10 is such that a predefined length of guide element corresponds to a quantity of beads sufficient to fill a predefined volume. For example, a given length of, for example, 5 cm of the guide element with beads may correspond to a volume of 1 cc. Thus, based on prior planning considerations of the total desired volume of the restored disc and the current volume, the corresponding required quantity of beads may be determined simply by marking-off a required length of the bead-carrying guide element to be used, and possibly severing the beads from the guide element beyond that length.

Once the desired expansion of the intervertebral disc has been achieved by insertion of the required quantity of beads, guide element 10 is removed and rigid tubes 12, 14 are withdrawn. Appendages 32 and 34 are then tied or otherwise sealed to prevent release of beads from net element 30. Appendages 32, 34 are then attached to ipsilateral regions of bone so as to: (a) seal the contents of the net inside the net; and (b) fix net element 30 in a required position. This bilateral fixation provides reliable positioning of the net element so as to avoid problematic migration of the disc filling from its intended place. The outer incisions may then be closed with adhesive tape to complete the surgical procedure.

Vertebral Body Height Restoration

Figure 8A:
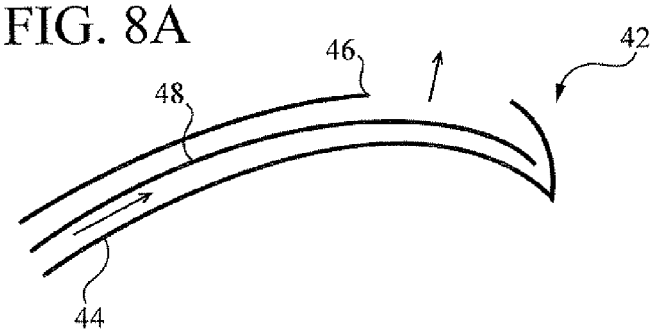
FIGS. 8A and 8B are schematic plan views illustrating a directional tissue compression device for use in a procedure on a vertebral body according to the teachings of the present invention, the device being shown prior to and during use, respectively.
Figure 8B:
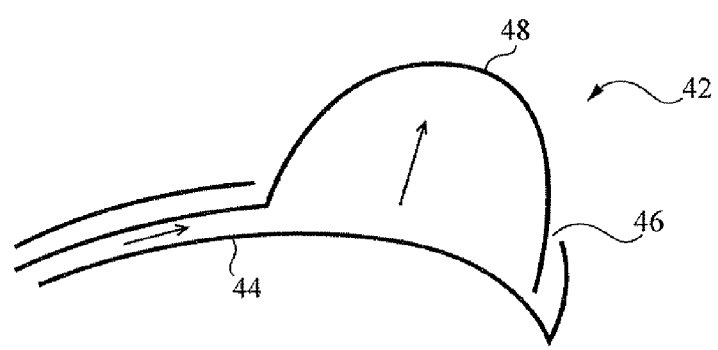
Figure 9:
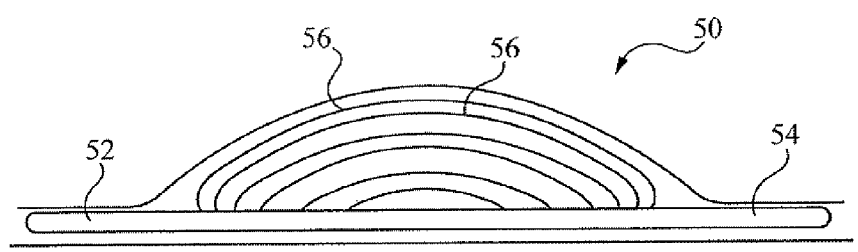
FIG. 9 is a schematic plan view of a directionally inflating perforated expandably fillable element, constructed and operative according to the teachings of the present invention, for use in a vertebral body subsequent to said direction tissue compression device.

Turning now to FIGS. 8A, 8B and 9, there is illustrated a preferred apparatus and technique for restoration of a collapsed or damaged vertebral body. Here too, although described in a particularly preferred context implemented using the surgical method of the present invention, various aspects of the apparatus and technique are believed to be patentable in their own right even if implemented using otherwise conventional surgical methods.

Generally speaking, the technique solves various problems associated with controlling expansion directions of inflatable elements by dividing the procedure into two stages. In a first stage, a directional tissue compression device is introduced into the vertebral body and operated to apply pressure to a transverse slice of tissue within the vertebral body so as to form a cavity anterior to the guide element. Then, once a slice-shaped cavity is formed, an expandably fillable element is introduced into the cavity and inflated with a filling material so as to increase an axial dimension of the vertebral body.

The technique of the present invention also addresses a further problem of cement leakage common to conventional procedures. Specifically, conventional vertebral body height restoration techniques typically employ an inflatable balloon which is inserted temporarily in order to achieve the desired height restoration. The balloon is then deflated and removed, and PMMA or other cement is injected into the cavity from which the balloon was removed. Such techniques suffer from lack of control over the dispersion of the cement which may leak from the vertebral body, or may set with various sharp or abrasive surface features which may subsequently pose a risk of damage to adjacent tissue or blood vessels. In contrast, by employing a permanent filling material (such as cement) for the filling process, the location of the cement is well defined and limited by the expandably fillable element so as to protect against uncontrolled leakage of the cement beyond the vertebral body.

According to a further preferred feature of this aspect of the present invention, the expandably fillable element includes perforations dispersed over its surface such that the introducing a filling material releases a small proportion (typically less than 20%, and most preferably no more than 10%) of the filling material to enhance fixation of the expandably fillable element to the bone of the surrounding vertebral body.

In the preferred context of the surgical method described above, rigid tubes 12 and 14 are first inserted through respective bores drilled in first and second pedicles, respectively, of the vertebra requiring reconstruction. Directional drilling is then typically used to form a channel across the gap between distal ends of the tubes, and guide element 10 is inserted through the vertebral body passing in through the first pedicle of the vertebra, across within the vertebral body and out through the second pedicle of the vertebra.

As mentioned earlier, a directional tissue compression device is then used to apply pressure to a transverse slice of tissue within the vertebral body so as to form a cavity anterior to the guide element. Most preferably, the device is guided by connection to guide element, although a free standing device may optionally be introduced even before insertion of the guide element. FIGS. 8A and 8B illustrate a particularly simple but effective preferred embodiment of the direction tissue compression device, designated 42. Device 42 includes a relatively rigid housing 44 with an arcuate form and having a lateral opening 46 formed near its tip. Housing 44 typically has a rectangular cross-sectional shape, although other shapes such as an oval shape are also possible. Some degree of flexibility may be required to allow housing 44 to be inserted along rigid tube 12. Within housing 44 is deployed a flexible strip. The mechanical properties of a flat strip are that it is relatively flexible for in-plane bending but resistant to sideways bending or torsional distortion. As a result, as the flexible strip 48 is advanced, confined within housing 44, it tends to bulge outwards directionally from opening 46 as shown in FIG. 8B, thereby applying pressure directionally to a slice of cancellous bone tissue lying anterior to the device (i.e., forward from the guide element and away from the spinal cord) and bounded by an outer arcuate profile, so as to open a corresponding slice-shaped cavity.

In this context, it should be noted that the term "slice" or "slice-shaped" is used herein in the description and claims to refer to any three-dimensional form bounded in part by two substantially parallel, substantially planar faces, and independent of the shape of the remaining boundaries. In the case of a cavity or void, the bounding surfaces are clearly the inward facing surfaces of the surrounding material. The term "height" and "axial" are used to refer to a dimension and direction, respectively, substantially parallel to the spinal cord. The term "transverse" is used to refer to a plane substantially perpendicular to the spinal cord.

Many suitable materials may be used to implement device 42, as will be apparent to one ordinarily skilled in the art on the basis of straightforward criteria of biocompatibility and the required physical properties. Preferred examples include various polymer materials and metals or metal alloys. Optionally, both housing 44 and flexible strip 48 may be formed from the same material with the differing degrees of flexibility being provided by suitable design of the dimensions and/or structure of the elements.

Once the slice cavity has been formed, an expandably fillable element is introduced into the cavity. A preferred implementation of an expandably fillable element, designated 50, is shown here schematically in FIG. 9. It should be noted that there is a particular synergy between the use of directional tissue compression device 42 and expandably fillable element 50 as described. Specifically, because of the presence of the well defined preformed slice cavity, the expandably fillable element expands during filling to initially deploy itself evenly over a large proportion of the lateral dimension of the vertebral body, thereby ensuring that the subsequent continued expansion acts substantially uniformly to increase an axial dimension of the vertebral body.

Most preferably, expandably fillable element 50 includes a pair of flexible elongated fixation appendages 52, 54 for providing precise positioning of expandably fillable element 50 prior to inflation and bilateral fixation on completion of the procedure, all in a manner analogous in that of appendages 32, 34 described above. Typically, one or both of appendages 52 and 54 serves also as a filling conduit for introducing filling material into expandably fillable element 50.

A wide range of biocompatible filling materials may be used to inflate expandably fillable element 50. The filling material may be a liquid, a gel, a paste or powdered or granulated solids. Preferred examples include, but are not limited to, PMMA and other cements or inert fillers, and/or various material or medicaments used for promoting bone growth or regeneration.

Most preferably, expandably fillable element 50 includes a plurality of perforations 56 such that a small proportion of the filling material is released from the surface of expandably fillable element 50 during the filling process to enhance fixation of the expandably fillable element in the surrounding tissue. The size of the perforations are chosen according to the physical properties of the filling material in order to ensure that only a small proportion is released. This fixation enhancement may be an immediate, or nearly immediate mechanical anchoring effect such as in the example of a bone cement filler, or may be part of a slower physiological process such as in the case of a bone regenerating material.

Arcuate Tunneling System

Turning now to FIGS. 10A-15, there is illustrated a further aspect of the present invention which provides a tunneling system for forming an arcuate tunnel through biological tissue. This system is applicable to a wide range of applications in orthopedic and other types of surgery where it is desired to form an arcuate channel through biological tissue at some point within a human or animal body. Particularly in the context of the MISS procedures of the present invention, the system may be used to advantage for forming a channel to bridge the gap between rigid tubes 12, 14. While it will be described by way of a non-limiting example in the aforementioned context, it should be appreciated that the system may be adapted, including scaling up or scaling down of dimensions, and adjustment of cross-sectional shape and/or radius of curvature, for use in other contexts.

Figure 10A:
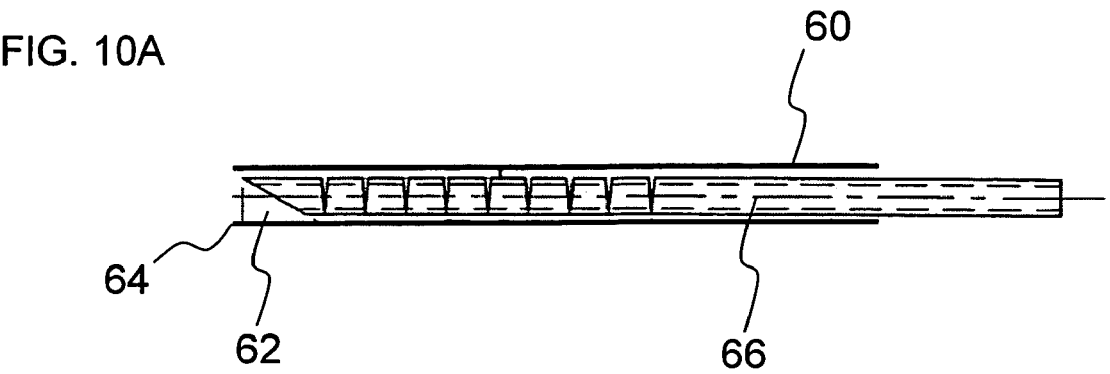
FIGS. 10A and 10B are schematic side views of a tunneling system, constructed and operative according to a further aspect of the present invention, shown prior to and during formation of an arcuate tunnel, respectively.
Figure 10B:
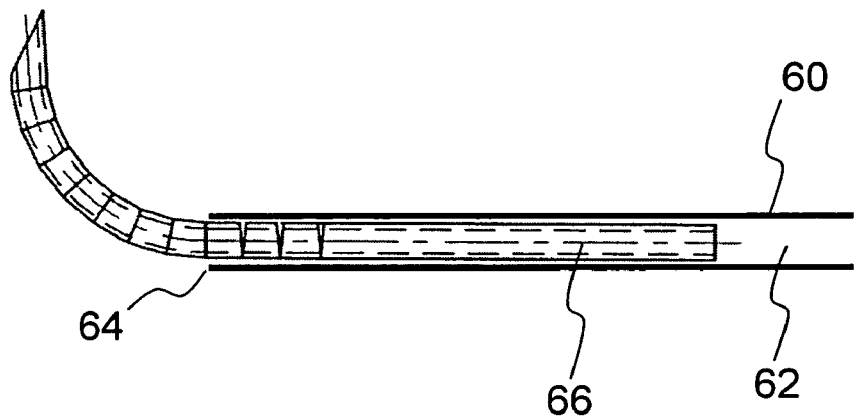
Figure 10C:
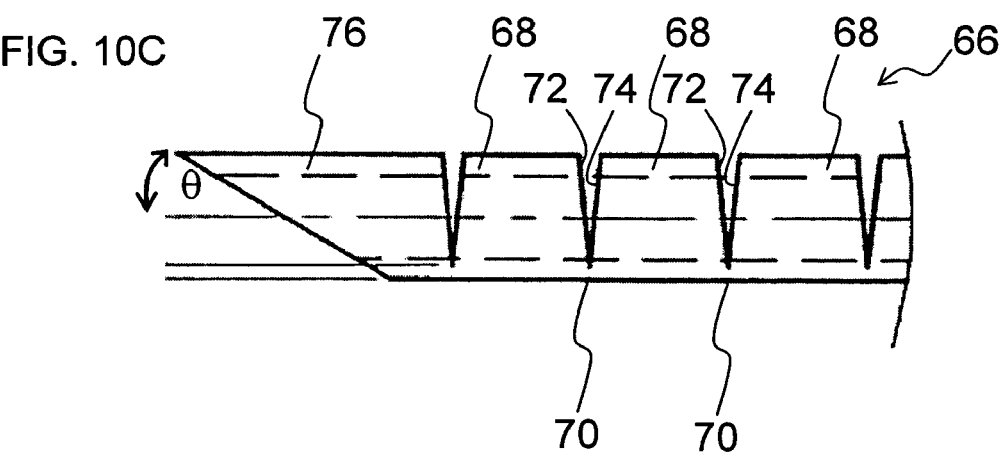
FIG. 10C is an enlarged view of a portion of a tunneling device from the tunneling system of FIG. 10A.

Referring now to FIGS. 10A, 10B and 10C, in general terms, the tunneling system includes a delivery conduit 60 having an inner channel 62 and an open end 64. At least part of inner channel 62 is substantially straight, meaning that it is either straight or at least has a radius of curvature significantly greater than that of the arcuate channel to be formed. Slidingly deployed within inner channel 62 is a tunneling device 66. As best seen in FIG. 10C, at least a distal portion of tunneling device 66 is formed from a series of substantially rigid elements 68 interconnected at pivotal interconnection regions 70 which are configured to transfer compressive forces between adjacent of the elements and provide a series of parallel effective hinge axes. Each element 68 also exhibits at least one contact surface 72 disposed for abutting a corresponding region 74 of an adjacent one of elements 68 so as to define a maximum deflection of relative pivotal motion between adjacent of the elements. The result of this structure is that, when the distal portion of tunneling device 66 is deployed within inner channel 62, at least part of the distal portion assumes a substantially straight state (FIG. 10A) with contact surfaces 72 and the corresponding regions 74 separated. Then, as the distal portion is advanced beyond open end 64 into the biological tissue, elements 68 are deflected to the maximum deflection so that a part of the distal portion beyond open end 64 assumes a pre-defined substantially arcuate state (FIG. 10B).

At this stage, it will be appreciated that the tunneling system of the present invention provides a particularly elegant and effective solution for forming an arcuate tunnel through tissue. Specifically, the substantially straight state of the tunneling device allows it to be inserted along a straight delivery conduit to reach the desired location within the body for starting the arcuate channel. As the tunneling device advances from the delivery conduit, resistance of the tissue itself, optionally supplemented or replaced by a mechanical biasing arrangement, causes elements 68 to close against each other, thereby forming a mechanically stable arcuate formation which can be driven from the rear by a compressive driving force to forcibly generate an arcuate channel through the tissue. This and other advantages of the tunneling system of the present invention will become clearer from the following description.

It will be noted in this context that the pivotal interconnection regions 70 may be implemented in many different ways. By way of non-limiting examples, according to a first option, the interconnection regions are hinge structures which attach separately formed elements 68. According to a second option, discrete elements 68 are attached along a common flexible backing strip. According to a third option, the interconnection regions are integrally formed with elements 68. In the latter case, the structure is preferably integrally formed as an elongated body with a plurality of transverse slots spaced along its length. Regions between adjacent slots thus provide substantially rigid elements 68 and regions around the slots providing the pivotal interconnection regions 70. In the case of metal or metal alloy implementations (referred to generically as "metallic material"), this is typically implemented by machining a length of solid material or a hollow profile to form transverse slots. In the case of polymer materials, the entire structure may be integrally molded or formed by other conventional polymer production techniques.

Where reference is made herein to "parallel effective hinge axes" it will be noted that this includes both well defined hinge axes such as that of a hinge-pin structure and a distributed flexion hinge where a relatively thin region of flexible material provides freedom of pivotal movement. In the latter case, the effective hinge axis is defined herein as the axis of a hinge-pin structure which would most closely approximate the pivotal freedom of movement provided by the flexion hinge.

According to one preferred implementation, the tunneling device of the present invention has an open-ended hollow elongated body. In this case, the device operates like an apple-core removing tool, punching out tissue lying in its arcuate path so that the tissue accumulates within the hollow profile of the device. To enhance this mode of operation, the leading edges which circumscribe the end of the opening of the hollow profile may be sharpened to form a cutting edge. This configuration is particularly suitable for tunneling through relatively soft tissue, such as for the repair of damaged intervertebral discs as described above with reference to FIGS. 5-7, although it is also useful for a wide range of other applications.

According to an alternative implementation, at least a distal tip of the tunneling device of the present invention is non-hollow. Optionally, the entire device may be formed from a solid block slotted as described above. An example of a non-hollow tunneling device is shown schematically in FIG. 15. This implementation is particularly suited for tunneling through cancellous bone, such as for the restoration of a collapsed or damaged vertebral body as described above with reference to FIGS. 8A, 8B and 9, although it is also useful for a wide range of other applications.

Tunneling device 66 may be implemented in a large number of cross-sectional shapes. In the preferred examples illustrated herein, the elongated body of the device has a substantially rectangular cross-sectional outline, optionally square. Alternative cross-sectional shapes include, but are not limited to, triangular, rhomboid, semicircular and otherwise-modified circular. In each case, the cross-sectional shape preferably has at least one flat side which serves as a base within which (or close to which) the hinge axes lie.

Figure 11A:
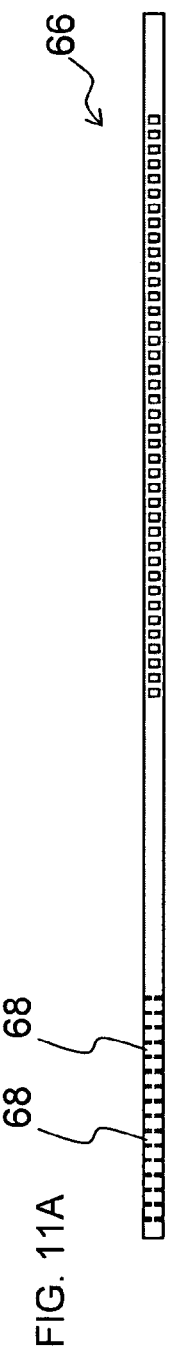
FIGS. 11A and 11B are top and side views, respectively, of a tunneling device suitable for use in the tunneling system of FIGS. 10A and 10B in a substantially straight state.
Figure 11B:
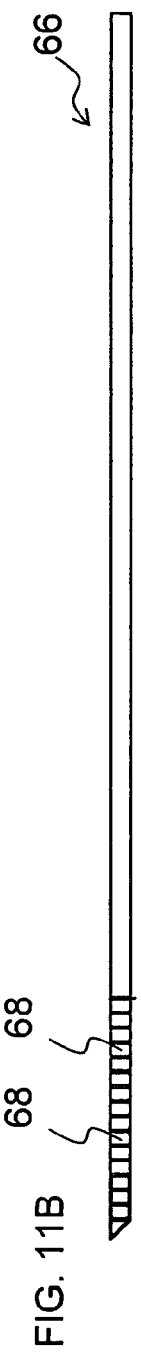
Figure 11C:
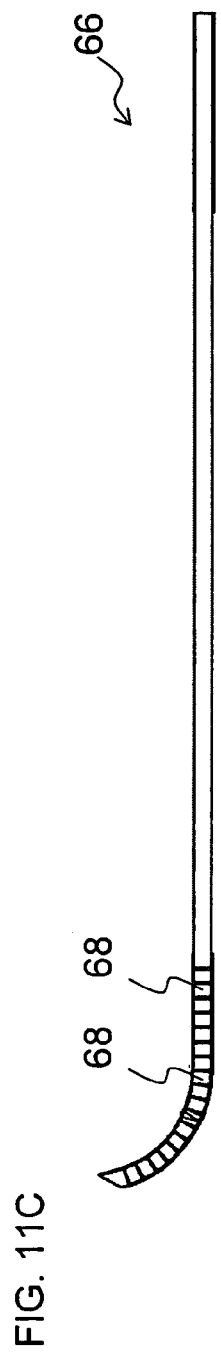
FIG. 11C is a view similar to FIG. 11B showing the tunneling device in an arcuate state.
Figure 11D:
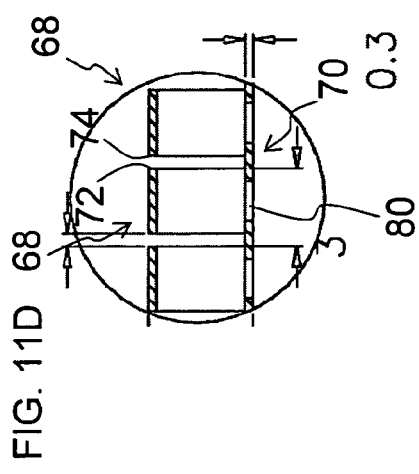
FIG. 11D is an enlarged cross-sectional view of a small region of FIG. 11B.
Figure 11E:
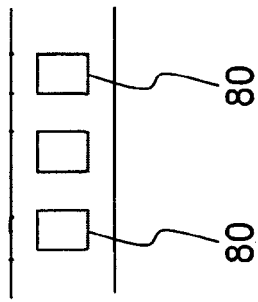
FIG. 11E is an enlarged view of a small region of FIG. 11A.

It will be noted that contact surfaces 72 and corresponding regions 74 may be implemented in many different ways so long as they provide a well defined maximum-deflection abutment position between adjacent elements 68. In a first non-limiting example as illustrated in FIGS. 10A-10C and 15, the contact surfaces and corresponding regions are defined by facing sides of transverse slots which are substantially V-shaped. In a second non-limiting example illustrated in FIGS. 11A-11E, the transverse slots are substantially parallel-sided, having either a rectangular or U-shaped form as viewed from the side (FIGS. 11B and 11D). Although the maximum deflection between adjacent elements 68 is typically the same for each pivotal interconnection, it should be noted that this is not essential so long as the fully deflected state approximates to an arc of a circle. Thus, deflection angles alternating between two values would also be acceptable.

Figure 13B:
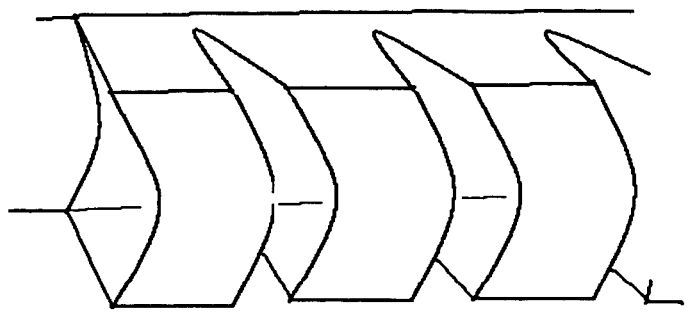
FIGS. 13A and 13B are schematic isometric views of a further alternative implementation of the tunneling device of FIGS. 10A and 10B in a substantially straight state, showing non-hollow and hollow implementations, respectively.
Figure 13A:
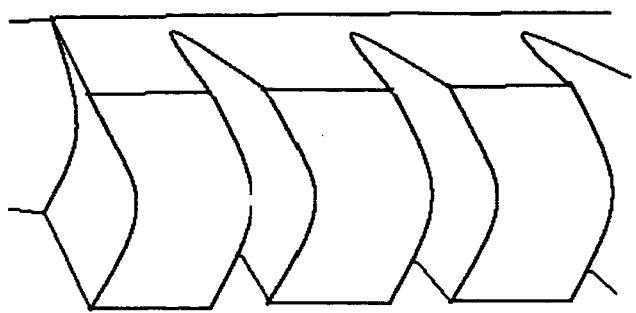
Figure 12B:
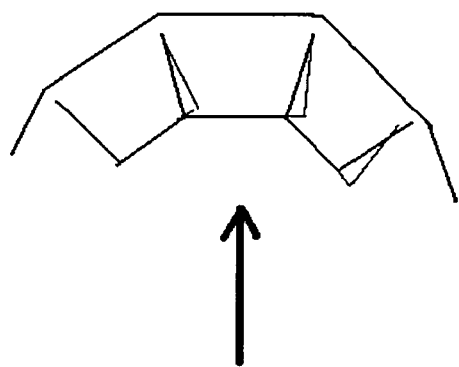
FIG. 12B is a side view of the device of FIG. 12A in an arcuate state.
Figure 12A:
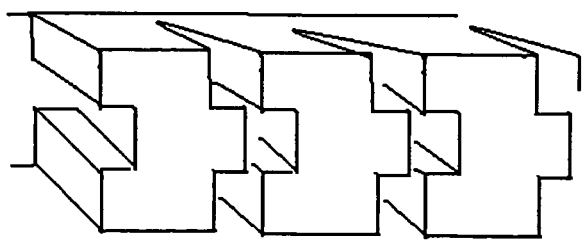
FIG. 12A is a schematic isometric view of an alternative implementation of the tunneling device of FIGS. 10A and 10B in a substantially straight state.

Turning now to FIGS. 12A-13B, according to a further preferred option, contact surfaces 72 and corresponding regions 74 are configured to provide some degree of interlocking, particularly configured to offer resistance against lateral or torsional displacement of adjacent elements 68. To this end, each element 68 preferably features at least two non-coplanar contact surfaces 72 and corresponding regions 74. In a first example shown in FIG. 12A, the contact surfaces define an angular ridge and the surfaces of corresponding regions 74 define a complementary trough. This provides a positive interlocking structure in the arcuate state, as indicated by the dashed lines showing overlap in FIG. 12B. In the alternative implementations of FIGS. 13A and 13B, a similar concept is implemented using a shallower V-shape form as viewed from above (i.e., from the side furthest from pivotal interconnection regions 70). Here too, the non-coplanar deployment of the abutment surfaces provides some degree of interlocking, resulting in enhanced stability against lateral motion and torsion. Clearly, this principle is applicable both to solid (non-hollow) elements 68 as shown in FIG. 13A and hollow elements 68 as shown in FIG. 13B.

In order to ensure deflection of the tunneling device into its arcuate form as it advances, tunneling device 66 preferably terminates in a distal tip 76 having a bevel angle θ inclined so as to tend to deflect the elements towards its arcuate state when advanced. Bevel angle θ, defined as the angle between the plane of the beveled end surface and a longitudinal axis of the tunneling device when in the substantially straight state, is preferably between 20° and 70°. This beveled tip ensures that the device reliably assumes its arcuate state as it is advanced into biological tissue due to the resistance of the tissue itself.

Additionally, or alternatively, to the beveled distal tip 76, the tunneling device may include a tensioning element (not shown) deployed along at least part of a length of the tunneling device for biasing adjacent of the elements to the maximum deflection. This option is particularly valuable where tunneling device 66 is to pass through damaged tissue, or through a fluid-filled or open volume, where there may be insufficient mechanical resistance to reliably deflect the device to its arcuate position. The tensioning element may be implemented as a resilient cable extending along a channel within the tunneling device. Alternatively, a substantially non-stretchable cable may be used with manual or other actuation to selectively apply a force to deflect the device.

Figure 14:
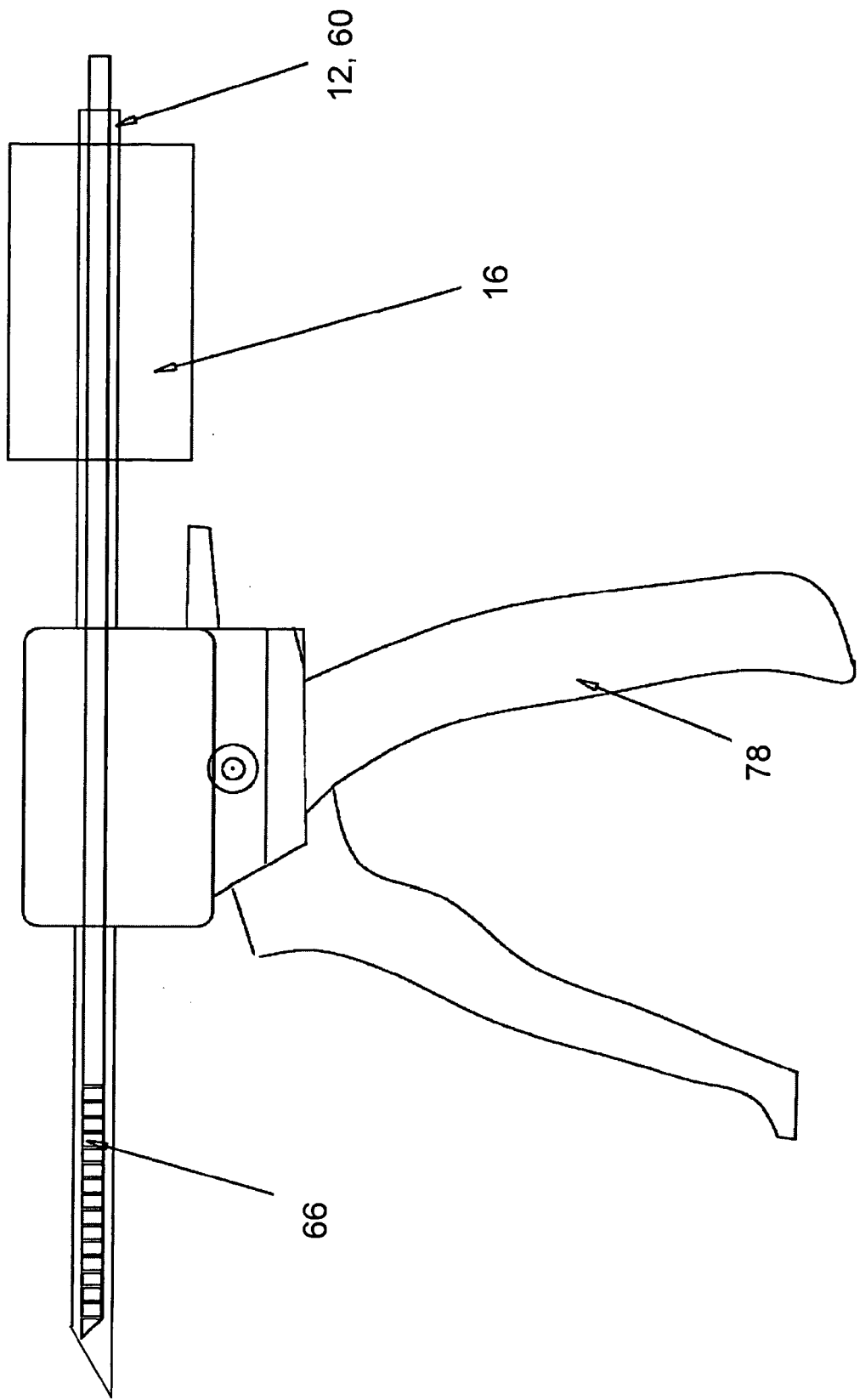
FIG. 14 is a schematic illustration of the tunneling system of FIGS. 10A and 10B for use in the apparatus of FIGS. 1-9 and including a drive device for advancing the tunneling device.
Figure 15:
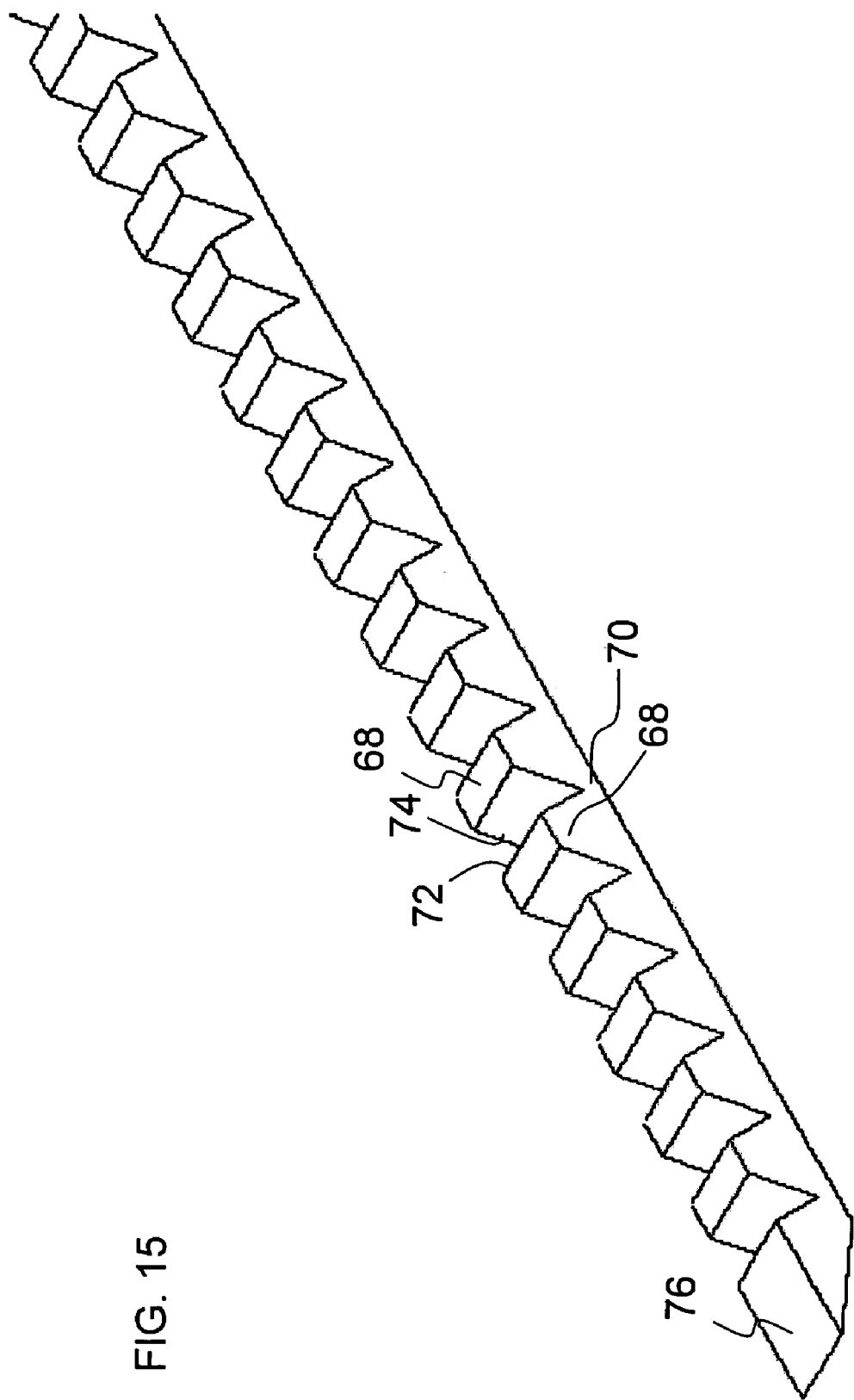
FIG. 15 is a schematic isometric view of a non-hollow implementation of the tunneling device of FIGS. 10A and 10B.

Turning finally to FIG. 14, the tunneling system of the present invention preferably further includes a drive device configured to advance the tunneling device relative to the delivery conduit. In the preferred example shown here, there is shown a manually operable drive device 78 configured such that repeated manual operation of a trigger handle causes stepwise advancing of tunneling device 66 relative to conduit 60. Most preferably, drive device 78 operates as a sprocket drive with at least one projecting feature (not shown) for engaging a corresponding series of recesses 80 (FIGS. 11D and 11E) formed along at least part of the length of tunneling device 66.

By way of a non-limiting preferred example, the tunneling system including drive device 78 is illustrated in FIG. 14 as part of the MISS apparatus of FIG. 1. In this case, conduit 60 may be implemented as hollow rigid tube 12 clamped by rigid coupling 16. For simplicity of presentation, the second hollow rigid tube 14 has been omitted here.

It will be appreciated that the above descriptions are intended only to serve as examples, and that many other embodiments are possible within the scope of the present invention as defined in the appended claims.

What is claimed is:

1. A tunneling system for forming an arcuate tunnel through biological tissue, the tunneling system comprising:
    (a) a rigid delivery conduit having an inner channel and an open end, at least part of said inner channel being substantially straight; and
    (b) a tunneling device for deploying within said inner channel and advancing beyond said open end, at least a distal portion of said tunneling device being formed from a series of substantially rigid elements interconnected at pivotal interconnection regions having parallel effective hinge axes, said interconnection regions being configured to transfer compressive forces between adjacent of said elements, each of said elements further including at least one contact surface disposed for abutting a corresponding region of an adjacent one of said elements so as to define a maximum deflection of relative pivotal motion between adjacent of said elements,
such that, when said distal portion is deployed within said inner channel, at least part of said distal portion is limited by said rigid delivery conduit to a substantially straight state with said contact surfaces and said corresponding regions separated and, as said distal portion is advanced beyond said open end into said biological tissue, said elements are deflected to said maximum deflection so that a part of said distal portion beyond said open end assumes a pre-defined substantially arcuate state while another part of said distal portion remaining within said delivery conduit is maintained in said substantially straight state.

2. The tunneling system of claim 1, wherein said tunneling device is integrally formed as an elongated body with a plurality of transverse slots spaced along its length, regions between adjacent of said slots providing said substantially rigid elements and regions around said slots providing the pivotal interconnection regions.

3. The tunneling system of claim 2, wherein said elongated body is formed from metallic material.

4. The tunneling system of claim 2, wherein said elongated body is hollow.

5. The tunneling system of claim 2, wherein at least a distal tip of said elongated body is non-hollow.

6. The tunneling system of claim 2, wherein said elongated body has a substantially rectangular cross-sectional outline.

7. The tunneling system of claim 2, wherein said transverse slots are substantially V-shaped.

8. The tunneling system of claim 2, wherein said transverse slots are substantially parallel-sided.

9. The tunneling system of claim 1, wherein each of said elements includes at least two of said contact surfaces and a corresponding two abutment regions, said at least two contact surfaces being non-coplanar.

10. The tunneling system of claim 1, wherein said tunneling device terminates in a distal tip having a bevel angle inclined so as to tend to deflect said elements towards said arcuate state when advanced.

11. The tunneling system of claim 10, wherein said bevel angle is inclined between 20° and 70° to a longitudinal axis of said tunneling device when in said substantially straight state.

12. The tunneling system of claim 1, further comprising a drive device associated with said delivery conduit and with said tunneling device, said drive device being configured to advance said tunneling device relative to said delivery conduit.

13. The tunneling system of claim 12, wherein said tunneling device features a series of recesses, said drive device having at least one projecting feature for engaging at least one of said recesses.

14. The tunneling system of claim 1, wherein said tunneling device further includes a tensioning element deployed along at least part of a length of said tunneling device for biasing adjacent of said elements to said maximum deflection.

15. An apparatus for use in performing a minimally invasive spinal surgical procedure via a pair of bilateral stab wounds on either side of a subject region of the spine of a patient, the apparatus comprising:

(a) a first hollow rigid tube having a proximal end and a distal end, said distal end for insertion through a first of the stab wounds;

(b) a second hollow rigid tube having a proximal end and a distal end, said distal end for insertion through a second stab wound in the back of a patient;

(c) a rigid coupling for rigidly coupling said first and second tubes such that said tubes converge towards said distal ends but maintain a predefined gap between said distal ends; and (d) a tunneling system deployable along said first tube for forming an arcuate tunnel so as to traverse said gap between said distal ends of said first and second tubes, said tunneling system including a tunneling device, at least a distal portion of said tunneling device being formed from a series of substantially rigid elements interconnected at pivotal interconnection regions having parallel effective hinge axes, said interconnection regions being configured to transfer compressive forces between adjacent of said elements, each of said elements further including at least one contact surface disposed for abutting a corresponding region of an adjacent one of said elements so as to define a maximum deflection of relative pivotal motion between adjacent of said elements, such that, when said distal portion of said tunneling device is deployed within said first tube, at least part of said distal portion assumes a substantially straight state with said contact surfaces and said corresponding regions separated and, as said distal portion of said tunneling device is advanced beyond said distal end, said elements are deflected to said maximum deflection so that a part of said distal portion of said tunneling element beyond said distal end of said first tube assumes a pre-defined substantially arcuate state.

16. The apparatus of claim 15, further comprising an elongated flexible guide element for deployment, after removal of said tunneling system, so as to extend through said first hollow tube from said proximal end to said distal end, to traverse said gap and to extend through said second hollow tube from said distal end to said proximal end.

17. The apparatus of claim 15, wherein said first and second tubes are implemented as substantially straight hollow tubes.

18. The apparatus of claim 15, wherein said distal ends of said first and second tubes are implemented as inward-facing beveled ends.

19. The apparatus of claim 15, wherein said distal ends of said first and second tubes are curved towards said gap.

20. The apparatus of claim 15, further comprising a removable trocar removably receivable within each of said first and second tubes for facilitating insertion of said first and second tubes in the back of the patient.

* * * * *